(12) United States Patent
Dorawa et al.

(10) Patent No.: US 8,057,480 B2
(45) Date of Patent: Nov. 15, 2011

(54) ULTRASONIC HANDPIECE

(75) Inventors: Klaus Dorawa, Schönkirchen (DE);
Manuel Schwager, Zurich (CH);
Marcel Aeschlimann, Ligerz (CH);
Philipp Seiler, Arboldswil (CH)

(73) Assignee: Stryker Trauma GmbH (DE)

( * ) Notice: Subject to any disclaimer, the term of this patent is extended or adjusted under 35 U.S.C. 154(b) by 1158 days.

(21) Appl. No.: 11/879,047

(22) Filed: Jul. 13, 2007

(65) Prior Publication Data
US 2009/0018471 A1    Jan. 15, 2009

(51) Int. Cl.
*A61B 17/58* (2006.01)
*A61C 1/07* (2006.01)
*A61C 3/03* (2006.01)

(52) U.S. Cl. ............ 606/92; 606/86 R; 606/99; 433/86; 433/119

(58) Field of Classification Search ............... 606/92–95; 433/86, 119
See application file for complete search history.

(56) References Cited

U.S. PATENT DOCUMENTS

| | | |
|---|---|---|
| 4,653,489 A | 3/1987 | Tronzo |
| 5,176,677 A | 1/1993 | Wuchinich |
| 5,993,458 A | 11/1999 | Vaitekunas et al. |
| 6,561,983 B2 | 5/2003 | Cronin et al. |
| 2002/0031744 A1* | 3/2002 | Mossle et al. .............. 433/119 |
| 2004/0030341 A1 | 2/2004 | Aeschlimann et al. |
| 2004/0038180 A1 | 2/2004 | Mayer et al. |
| 2006/0105295 A1 | 5/2006 | Mayer et al. |
| 2006/0122624 A1 | 6/2006 | Truckai et al. |
| 2006/0264787 A1 | 11/2006 | Yamada et al. |

FOREIGN PATENT DOCUMENTS

| | | |
|---|---|---|
| EP | 0 424 231 | 4/1991 |
| EP | 1 808 139 | 7/2007 |
| WO | 00/72766 | 12/2000 |
| WO | 2004/004543 | 1/2004 |
| WO | WO-2007/014142 | 2/2007 |

* cited by examiner

*Primary Examiner* — Thomas C. Barrett
*Assistant Examiner* — Michael T Schaper
(74) *Attorney, Agent, or Firm* — Lerner, David, Littenberg, Krumholz & Mentlik, LLP

(57) ABSTRACT

An ultrasonic handpiece is used for augmenting a bone screw. The handpieces comprise a housing, an ultrasonic converter shiftingly accommodated in the housing, and a sonotrode connected to one end of the ultrasonic converter. The sonotrode protrudes from the housing into the bone screw. An adjuster wheel is adjustably connected to the housing. A spring is provided the ends of which are supported by the ultrasonic converter and the adjuster wheel, respectively. The ultrasonic converter is preloaded in the direction away from the adjuster wheel by setting the adjuster wheel, thereby the sonotrode is urged with a selected force into the bone screw and the augmentation material is pressed out of the bone screw and into the bone.

10 Claims, 1 Drawing Sheet

ULTRASONIC HANDPIECE

BACKGROUND OF THE INVENTION

The invention relates in general to sonic fusion technology, it relating more particularly to an ultrasonic handpiece and a method for use thereof.

Known from U.S. Pat. No. 4,653,489 is a system wherein a fixation cement is introduced through a bone screw into a portion of a bone afflicted by osteoporosis. Femoral neck fractures as well as distal femoral fractures can be fixated by means of this system.

The system in accordance with prior art comprises a bone screw having a flow cavity, i.e. an axial through bore through which bone cement can be introduced into the portion at the tip of the screw. The bone cement is advanced by a device which is releasably attached to the trailing end of the screw. This device is similar to a commercially available syringe in comprising substantially a cylindrical barrel and a plunger. The barrel forms a cavity in which the plunger is movable to and fro.

In use of this prior art device the fixation cement is filled into the barrel, after which the plunger is urged against the cement. By applying manual compression force the fixation cement is jetted into the axial through bore of the bone screw. Due to the pressure the fixation cement is adequately fluidized so that it can pass through the proximal end of the bone screw into the bone, as a result of which the bone screw is augmented in the bone.

This system has the drawback that the manual pressure applied to the fixation cement varies, not only basically from application to application but also during the application itself so that the distribution of the fixation cement within the portion of the bone at the tip of the bone screw is neither reliable nor even.

SUMMARY OF THE INVENTION

An aspect of the invention is to define a device and a method by which a reliable and even augmentation of a bone screw at an implantation site in the bone can now be assured.

One aspect is achieved in accordance with the invention by the ultrasonic handpiece having a housing having a first and second end. An ultrasonic sonotrode converter is mounted within the first end of the housing for reciprocal movement within the housing. An adjuster wheel is adjustably connected to the second end of the housing by a threaded connection. An elastic element or spring has a first end which engages the ultrasonic converter and a second end which engages the adjuster wheel. Adjusting the location of the adjuster wheel in an axial direction of the housing applies a preload on the ultrasonic converter. Another aspect is achieved by a method of using the ultrasonic handpiece as described above comprising securing the first end of the housing to an implant. The sonotrode protrudes into the implant. A force is applied on the ultrasonic converter by adjusting the axial position of the adjuster wheel. A polymeric rod is inserted into the implant and the ultrasonic converter activated so that the polymeric rod liquefies. The ultrasonic converter is then deactivated and the housing is released from the polymerically augmented implant. A bone screw which may be used with this handpiece is disclosed in a U.S. patent application filed on Jul. 13, 2007 entitled "Device For The Fixation Of Bone Fractures" listing Klaus Dorawa and Manuel Schwager as inventors the disclosure of which is incorporated herein by reference.

BRIEF DESCRIPTION OF THE DRAWINGS

The invention will now be detailed by way of a preferred embodiment with reference to the attached drawings in which.

DETAILED DESCRIPTION

Figure 1:
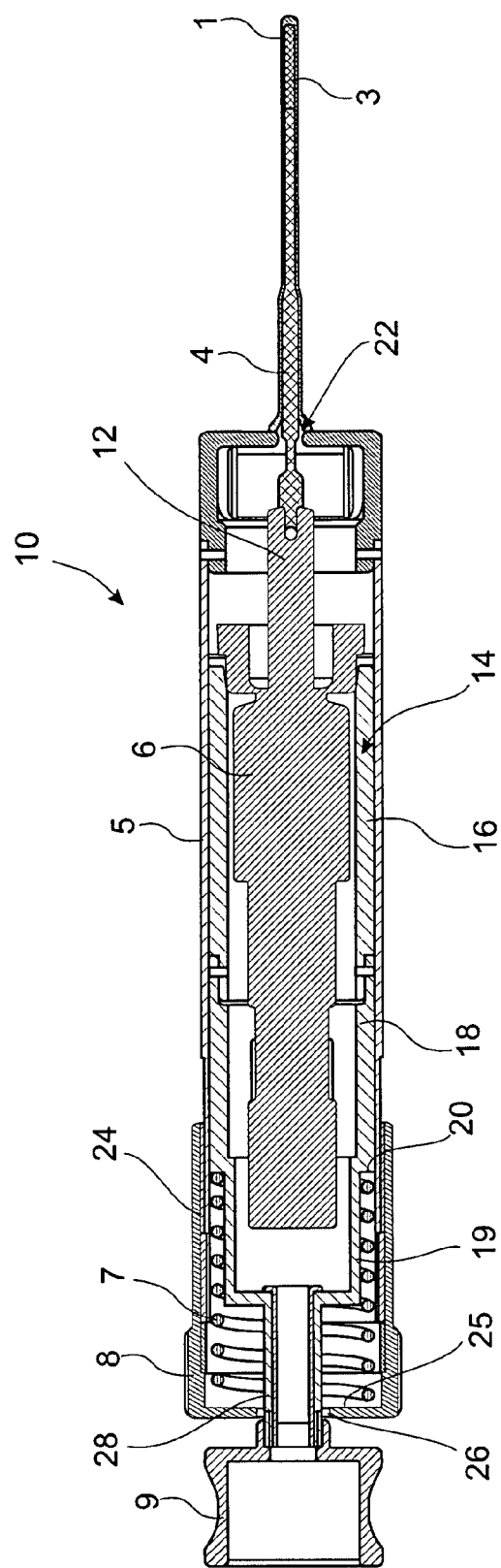
FIG. 1 is a section view of an ultrasonic handpiece in accordance with one embodiment of the invention.

Referring now to FIG. 1 there is illustrated an ultrasonic handpiece in accordance with a preferred embodiment of the invention generally denoted as 10. The core element of the ultrasonic handpiece is an ultrasonic converter 6. This converter is electrically powered, receiving either line power or rechargeable as well as not rechargeable battery power (not shown). At its one end the converter features a tip 12 which is caused to vibrate by means of converter 6. To transmit the vibrations to an element located remote from the ultrasonic handpiece a sonotrode 4 is secured to tip 12.

The body of the converter 6 is accommodated in a two-piece housing 14. The one part 16 of the converter housing 14 adjoining tip 12 is connected to the converter body and the other part 18 of body 14 which closes off the converter body comprises at its outer side a step 20 mounting one end of an elastic element such as a coil spring 7 in the axial direction of the converter. This spring also receives side support and guidance by the configuration of the end 19 of the second housing part 18. Instead of the coil spring some other preloading means such as a rubber buffers, leaf springs or the like could be employed. Furthermore, coil spring 7 may be a compression spring or tension spring.

In addition, the ultrasonic handpiece comprises an outer housing 5 in which the ultrasonic converter 6 is accommodated together with its converter housing 14. The ultrasonic converter 6 can be axially reciprocated together with the converter housing 14 in the housing 5. The vibrations generated by converter 6 are damped in this arrangement and transmitted to a user's hand holding the housing 5. The housing 5 comprises at its one end an aperture 22 through which sonotrode 4 protrudes outwardly. Also provided at this end is a means, a thread for example, for securing an implant or also a bone screw into which the sonotrode 4 extends, when the implant or the bone screw is fixedly connected to the ultrasonic handpiece.

At its other end the housing 5 comprises a thread 24 around its outer surface. Screwed onto thread 24 is an adjuster wheel 8 substantially configured as a screw cap, such that the second end of the coil spring 7 is supported at the inner side 25 of adjuster wheel 8. By means of adjuster wheel 8 the spring 7 can be preloaded. By means of a rotation of adjuster wheel 8 on housing 5, the adjuster wheel will move in the axial direction of the housing. Accordingly spring 7, supported between adjuster wheel 8 and step 20 of housing part 18, will be compressed or expanded. The travel in of the spring and thus the displacing of housing 14 and converter 6 axially within the housing 5 is preferably 30 mm and is generally in the range 10 mm to 50 mm, although this too can be dimensioned optionally as required. Provided in the adjuster wheel 8 axially is an aperture 26 through which a reduced end portion 28 of the second housing half 18 of the converter housing 14 protrudes outwardly. Secured to end 19 of second housing half 18 is a stop which limits the travel of the ultrasonic converter 6 in the housing 5, this likewise limiting the travel of the sonotrode connected to the ultrasonic converter relative to the housing 5 and the implant 1 connected thereto.

Use of the ultrasonic handpiece in augmenting a bone screw in a bone will now be detailed. Firstly, a guide wire such as a K wire is powered up to a site in a bone at which the bone screw is to be located. Via the K wire the bone screw is advanced and then screwed into place until it is positioned as desired. The K wire is then removed after having sited the bone screw in the bone. After withdrawal of the K wire a passageway is free along the longitudinal center line of the bone screw. A polymer pin 3 together with a metal insert is then introduced into the free passageway.

When the housing 5 of the ultrasonic handpiece is then connected to the bone screw the sonotrode 4 protrudes into the bone screw, the distal end of the sonotrode coming into contact with the polymer pin 3. By means of the adjuster wheel 8 a defined compression force can be set acting from the sonotrode on the polymer pin. The preload can be temporarily fixed for example by a block clamped in place between the adjuster wheel and the stop 9. This block must, however, first be removed before the ultrasonic converter is switched on.

On being switched on, the converter generates vibrations which together with the pressure generated by the spring preloaded between the converter housing and the adjuster wheel and acting on the polymer pin, ensure that the material of the polymer pin is fluidized, resulting in the material of the polymer pin being pressed out of the tip of the bone screw. It is in this way that the bone screw is augmented in the bone.

The ultrasonic handpiece in accordance with the invention has the following advantages. Firstly, a defined compression force is now reproducibly exerted on the polymer pin together with ultrasonic vibration having a defined amplitude, resulting in reliable fluidization of the polymer material. Secondly, the sonotrode is advanced by a specific travel into the bone screw, by way of which the amount of material to be pressed out of the bone screw into the bone is controlled.

It is to be noted that variants of any of the individual components may be combined with variants of other components in thus not being restricted to the combination as referred to concretely.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of using an ultrasonic handpiece to augment an implant comprising:
    obtaining an ultrasonic handpiece comprising a housing having a first and second end, an ultrasonic converter mounted within the first end of the housing for reciprocal movement within the housing in an axial direction of the housing, a sonotrode connected to one end of the ultrasonic converter and protruding out of the first end of the housing, an adjuster wheel adjustably connected to the second end of the housing, and an elastic element, a first end of which engages the ultrasonic converter and a second end of which engages the adjuster wheel, wherein adjusting the location of the wheel in an axial direction of the housing applies a preload on the ultrasonic converter, and wherein the ultrasonic converter is movable within the housing in the axial direction of the housing when a force acts on the sonotrode in the axial direction of the housing;
    securing the first end of the housing to the implant, the sonotrode protruding into the implant;
    applying a force on the ultrasonic converter by adjusting the axial position of the adjuster wheel;
    inserting a polymeric rod into the implant;
    activating the ultrasonic converter so that the polymeric rod liquefies;
    deactivating the ultrasonic converter; and
    releasing the housing from the implant.

2. The method as set forth in claim 1 wherein an inner surface of the adjuster wheel and an outer surface of the housing include mating threads which permit the adjustment of the adjuster wheel.

3. The method as set forth in claim 1 wherein the elastic element comprises a coil spring or a rubber buffer.

4. The method as set forth in claim 1 wherein the ultrasonic handpiece further comprises a stop connected to the ultrasonic converter which limits the displacement of the ultrasonic converter in the housing.

5. A method of using an ultrasonic handpiece to augment an implant comprising:
    obtaining an ultrasonic handpiece comprising a fixed first housing extending along a longitudinal axis having a first and second end, a second housing accommodated within the first housing for reciprocal movement therein along the longitudinal axis, an ultrasonic converter mounted within the second housing, an adjuster wheel adjustably connected to the second end of the first housing and moveable along the longitudinal axis, and an elastic element, a first end of which engages the second housing and a second end of which engages the adjuster wheel, wherein adjusting the location of the adjuster wheel along the longitudinal axis towards the second housing compresses the elastic element and applies a preload on the ultrasonic converter in the direction of the longitudinal axis;
    securing the first end of the housing to the implant, a sonotrode protruding into the implant;
    applying a force on the ultrasonic converter by adjusting the axial position of the adjuster wheel;
    inserting a polymeric rod into the implant;
    activating the ultrasonic converter so that the polymeric rod liquefies;
    deactivating the ultrasonic converter; and
    releasing the housing from the implant.

6. The method as set forth in claim 5 wherein an inner surface of the adjuster wheel and an outer surface of the first housing have mating threads to permit the adjustment of the adjuster wheel.

7. The method as set forth in claim 5 wherein the elastic element comprises a coil spring or a rubber buffer.

8. The method as set forth in claim 5 wherein the ultrasonic handpiece further comprises a stop connected to the ultrasonic converter and limiting the displacement of the second housing in the first housing.

9. The method as set forth in claim 5 wherein the sonotrode is connected to one end of the ultrasonic converter which sonotrode protrudes from the first end of the first housing.

10. The method as set forth in claim 5 wherein the adjuster wheel can be adjusted on the first housing 10 mm to 50 mm along the longitudinal axis.

* * * * *